(12) United States Patent
Wasden et al.

(10) Patent No.: US 6,964,642 B2
(45) Date of Patent: Nov. 15, 2005

(54) APPARATUS FOR BONE CONDUCTION THRESHOLD HEARING TEST

(75) Inventors: Christopher L. Wasden, Sugar Land, TX (US); Aaron Thornton, West Des Moines, IA (US)

(73) Assignee: Tympany, Inc., Stafford, TX (US)

(*) Notice: Subject to any disclaimer, the term of this patent is extended or adjusted under 35 U.S.C. 154(b) by 0 days.

(21) Appl. No.: 10/438,751

(22) Filed: May 15, 2003

(65) Prior Publication Data

US 2004/0073135 A1 Apr. 15, 2004

Related U.S. Application Data (60) Provisional application No. 60/383,303, filed on May 23, 2002, provisional application No. 60/466,313, filed on Apr. 29, 2003.

(51) Int. Cl.[7] ............................................. A61B 5/00
(52) U.S. Cl. ..................... 600/559; 73/585; 381/151; 381/326
(58) Field of Search . 600/559, 25; 73/585; 607/55–57; 381/150–151, 326, 380, 60; 267/42–46, 158

(56) References Cited

U.S. PATENT DOCUMENTS

| | | | |
|---|---|---|---|
| 3,134,861 A | * 5/1964 | Dempsey et al. | ........... 381/326 |
| 5,323,468 A | * 6/1994 | Bottesch | ...................... 381/151 |
| 5,645,074 A | 7/1997 | Shennib et al. | |
| 5,811,681 A | 9/1998 | Braun et al. | |
| 6,160,893 A | 12/2000 | Saunders et al. | |
| 6,331,164 B1 | 12/2001 | Shaw et al. | |
| 6,366,863 B1 | 4/2002 | Bye et al. | |
| 6,379,314 B1 | 4/2002 | Horn | |
| 6,396,930 B1 | 5/2002 | Vaudrey et al. | |
| 6,416,482 B1 | 7/2002 | Braun et al. | |
| 6,428,485 B1 | 8/2002 | Rho | |
| 6,447,461 B1 | 9/2002 | Eldon | |
| 6,644,120 B1 | 11/2003 | Braun et al. | |
| 2002/0016554 A1 | 2/2002 | Iseberg | |
| 2002/0026125 A1 | 2/2002 | Leysieffer | |
| 2002/0068986 A1 | 6/2002 | Mouline | |
| 2002/0076056 A1 | 6/2002 | Pavlakos | |
| 2002/0165466 A1 | 11/2002 | Givens et al. | |
| 2003/0083591 A1 | 5/2003 | Edwards et al. | |

FOREIGN PATENT DOCUMENTS

| | | | | |
|---|---|---|---|---|
| JP | 05030599 A | * | 2/1993 | ........... H04R 25/00 |
| NL | 8400196 | | 8/1984 | |
| WO | WO98/41973 | | 9/1998 | |
| WO | WO01/06916 | | 2/2001 | |
| WO | WO02/062221 | | 8/2002 | |

OTHER PUBLICATIONS

Gelfand, S.A., Essentials of Audiology, 2d ed., chapters 1, 3-7, and 11, Thieme Medical Publishers, Inc. (2001).

(Continued)

Primary Examiner—Max F. Hindenburg
Assistant Examiner—Sadaf Toor
(74) Attorney, Agent, or Firm—Conley Rose, P.C.

(57) ABSTRACT

An apparatus for bone conduction hearing testing is provided. The apparatus comprises a planar spring having opposed first and second elements to which are coupled, respectively, a bone conduction vibrator and an engagement element. The bone conduction vibrator contacts a first head portion, preferably the forehead, and the engagement element contacts a second head portion, preferably the rear of the head. The spring preferably has a lenticular shape, and may be either biconvex or D-shaped.

28 Claims, 7 Drawing Sheets

OTHER PUBLICATIONS

PCT/US03/16200 dated Jul. 28, 2004, search report.

International Search Report, PCT/US2003/016180 dated Oct. 6, 2003.

Gerald A. Studebaker et al., *Frequency-Importance and Transfer Functions for Recorded CID W-22 Word Lists,* Journal of Speech and Hearing Research; Apr. 1991, pp. 427-438, vol. 34.

Aaron R. Thornton et al., *Speech-Discrimination Scores Modeled As A Binomial Variable,* Journal of Speech and Hearing Research, Sep. 1978, pp. 507-518, vol. 21, No. 3.

Chris Haplin, Ph.D. et al., *The Articulation Index In Clinical Diagnosis and Hearing Aid Fitting,* Current Opinion in Otolaryngology & Head and Neck Surgery, 1996, pp. 325-334, Rapid Science Publishers.

*The Audiology Primer for Students and Health Care Professionals,* Summer 1997, pp. 1-69, Department of Veterans Affairs.

Aaron Thornton, *Computer-Assisted Audiometry and Technicians in a High-Volume Practice,* Nov. 1993 AJA, p. 11-13.

S. Joseph Barry, Can Bone Conduction Thresholds Really Be Poorer Than Air?, Nov. 1994 AJA, p. 21-22.

M.S. Dean and F.N. Martin, *Insert Earphone Depth and the Occlusion Effect,* American Journal of Audiology, vol. 9, 159-0889 (Sep. 5, 2000).

J.A. McCullough, R.H. Wilson, J.D. Birck and L.G. Anderson, *A Multimedia Approach for Estimating Speech Recognition of Multilingual Clients,* Mar. 1994 AJA, p. 19-22.

R.H. Wilson and J.K. Antablin, *A Picture Identification Task As An Estimate Of The Word-Recognition Performance of Nonverbal Adults,* Journal of Speech and Hearing Disorders, May 1980, vol. 45, No. 2.

* cited by examiner

APPARATUS FOR BONE CONDUCTION THRESHOLD HEARING TEST

CROSS-REFERENCE TO RELATED APPLICATION

This application for patent claims the benefit of priority from, and hereby incorporates by reference, U.S. Provisional Patent Application Ser. No. 60/383,303, entitled "Audiometer," filed on May 23, 2002, and U.S. Provisional Patent Application Ser. No. 60/466,313, entitled "System and Methods for Conducting Multiple Diagnostic Hearing Tests," filed on Apr. 29, 2003.

BACKGROUND OF THE INVENTION

1. Field of the Invention

This invention is directed in general to the field of audiological testing for human or animal patients, and more particularly to systems for conducting multiple diagnostic hearing tests to assess and analyze hearing loss in human patients. Systems of the invention provide an apparatus for reliably determining the air-conduction and bone-conduction hearing thresholds of a patient, and for conducting one or more additional tests involving acoustic immittance, otoacoustic emission, speech recognition threshold and speech discrimination. The systems further comprise components for performing such tests.

2. Description of the Related Art

Recent studies suggest that over 20 million people in the United States alone have some degree of hearing loss. The number of people worldwide who have some degree of hearing deficit is estimated to be much greater. Not surprisingly, many hearing-impaired people are unaware that they have suffered a decrease in hearing capacity. Because of the complexity of the hearing process itself, decreased hearing capacity may involve any of several factors, including age, health, occupation, injury, disease, and exposure to ototoxic agents, including some antibiotics. This loss of hearing can lead to significant reductions in quality of life, impaired relationships, reduced access to employment and diminished productivity.

Failure to treat the hearing loss may worsen its impact not only on the quality of life of the patient but also on economic productivity as a whole. According to the Better Hearing Institute, the annual cost in the United States in terms of lost productivity, special education, and medical care because of untreated hearing loss is approximately $56 billion. Much of this staggering cost could be reduced or prevented by early detection and treatment. Unfortunately, few people obtain regular and frequent hearing tests as a part of their routine healthcare due, at least in part, to the lack of a simple, convenient, and relatively inexpensive system for conducting hearing tests.

Traditionally, hearing tests are conducted in a clinical setting by a hearing health professional, such as an audiologist, who administers the hearing tests manually. In perhaps the most common type of testing, the hearing health professional controls an audiometer to produce a series of tones that each have a very specific frequency and intensity. The term "intensity" as used herein refers to the amplitude of the tone and is usually given in decibels (dB), expressed either as Sound Pressure Level (dB SPL), which is a logarithmic scale ratio of the intensity of a sound relative to a threshold value, usually $2 \times 10^{-2}$ N/m$^2$, or Hearing Level (db HL), which is a value normalized for a particular frequency to the threshold for patients with normal hearing. See, e.g., Gelfand, S., *Essentials of Audiology*, 2d ed., chapters 1, 3–6, Thieme Medical Publishers, Inc. (2001).

Because each of the tones has a specific frequency and intensity, this type of testing is known as "pure-tone" air conduction audiometry or "pure-tone threshold testing" for air conduction. Threshold testing may also be performed for bone conduction hearing and for speech recognition. In addition, related tests to determine speech discrimination capacity may also be performed. The foregoing types of testing, which involve providing a sound, such as a pure tone or speech, to the ear of the patient and determining whether the patient can hear or distinguish the sound, are referred to collectively as "audiometry," or "audiometric testing." Thus, air-conduction threshold, bone-conduction threshold, speech recognition threshold and speech discrimination tests are specific audiometric tests. Other types of hearing testing include acoustic immittance testing, which includes tympanometric testing and acoustic reflex testing, and otoacoustic emission testing. Such tests are well known in the art of hearing testing and are commonly performed by hearing health professionals.

In the typical manual protocol for pure-tone air-conduction threshold testing, electrical signals produced by the audiometer are converted into the desired pure tones by a transducer, such as earphones or ear inserts, located at or immediately adjacent to the ear of the patient, who is sequestered in a quiet room or sound isolation booth. For each audible tone, the patient gestures or otherwise indicates that he has heard the tone. If the tone is not audible, the patient does not respond. The hearing health professional thereafter adjusts the intensity level of the tone in preset increments until it becomes audible to the patient. By repeating this process for several different tones and compiling the results, the hearing health professional is able to determine the deviation of the patient's hearing threshold, at each frequency tested, from the reference hearing threshold established for normal hearing. The deviation of the threshold, if any, is a measure of the patient's hearing loss.

Manual administration of the pure-tone threshold test has certain advantages. Because the hearing health professional is physically present, he can apply his considerable training and experience during the test. For example, by simply talking to the patient and varying the loudness of his voice, the hearing health professional can determine an initial intensity level at which to start the tones and sounds. Furthermore, the hearing health professional can adapt the pace of the test as needed to accommodate a tired or uncooperative patient. Most importantly, the hearing health professional can discern between false responses or guesses and responses that are legitimate. Finally, the hearing health professional can adjust the results of the hearing test as needed to reflect extenuating circumstances or problems, such as excessive ambient noise, equipment limitations, and other similar factors.

Like most highly trained and specialized medical professionals, however, a hearing health professional's time and services are usually very expensive. Accessibility and convenience can also be issues, as there are fewer hearing health professionals relative to other types of medical professionals. And while hearing health professionals are highly trained, they are limited in their ability to make rapid and accurate calculations of the test data and have to rely on approximations and rules of thumb for guidance in many instances. In addition, few hearing health professionals in the United States can speak a foreign language and, therefore, traditional hearing tests are almost always administered in English, which can be a problem for non-English speaking patients.

Other drawbacks of the traditional, manually administered hearing tests include the need for a quiet room or sound isolation booth in order to properly conduct the tests. The quiet room or sound isolation booth has to comply with ANSI (American National Standards Institute) requirements in terms of how much ambient noise may penetrate the room or booth during a test. Typically, a specially trained technician must evaluate and certify the quiet room or sound isolation booth as meeting ANSI standards before the room or booth can be used. Such testing and/or certification is performed independently of the actual testing administered to a patient, and thus the actual ambient noise levels (and the reliability of the testing) during the testing of a given patient is unknown in current audiometric systems. In addition, there are at present relatively few technicians who are trained to perform such evaluations and certifications. All the above factors combine to increase the complexity of the traditional hearing tests and thereby discourage or at least contribute to a general lack of interest by most people in obtaining regular and frequent hearing tests.

One attempt to simplify the traditional hearing test involves the use of a computer network, such as the Internet, to administer the test. The computer network facilitates interaction between a centralized test administration site and remotely located patient sites. Such an arrangement makes it possible (or at least more convenient) for people in remote or rural areas to obtain a hearing test. The test can also be performed to meet standardized guidelines such as ANSI requirements or certification standards. Despite the increased convenience, however, a hearing health professional still has to manually administer the test, albeit remotely. In this regard, the test is very similar to the traditional hearing test and has many of the same shortcomings, in addition to the fact that the health professional is not physically present.

Accordingly, there is a need for a simpler, less expensive, and more convenient system for air-conduction threshold testing (and other types of hearing tests) that does not compromise the accuracy or thoroughness of the tests. In particular, there is need for an improved system to provide hearing tests that can be self-administered by the patient rather than by the hearing health professional, while retaining the advantages of having a skilled hearing health professional manually administer the test. There is also a need for a system for performing hearing tests that is capable of determining whether ambient noise levels are within acceptable levels during actual patient testing.

In addition to the foregoing limitations associated with audiometric testing, other particular testing limitations preclude widespread hearing testing. One such limitation involves bone-conduction hearing. Because the bones of the skull resonate in response to sound, hearing via bone conduction can be tested in a manner analogous to air conduction. However, instead of pure tones delivered by air conduction through earphones or loudspeakers, bone conduction hearing is tested by delivering sound through a bone-conduction vibrator coupled directly to a bone of the skull, usually the mastoid bone but in some instances the forehead.

Bone conduction testing is clinically significant because differences between the air-conduction and bone-conduction hearing thresholds provides an indication of how much of a hearing loss is attributable to the conductive structures in the outer and middle ear, and how much is attributable to the sensorineural structures of the inner ear and the auditory nerve. However, a reliable bone-conduction test apparatus has proven difficult to obtain because of equipment limitations. In particular, the vibrator element usually is encased in a protective plastic shell that is coupled to a holder, typically either a headset-type spring or a headband. Mastoid-placement bone conduction is particularly difficult because the anatomy of the mastoid makes slippage and/or shifting of the vibrator common. Physiological differences among patients, such as bone contours and fatty deposits in the area, are also more variable at the mastoid than the forehead. Even forehead-conduction bone testing may be difficult, however, not only because of insecure placement and slippage but also because of attenuation of the bone-conduction signal through the holder. Accordingly, there is a need for an improved bone-conduction test apparatus that provides consistent and secure placement, no attenuation, and reliable results.

There is a further need for a system capable of conducting multiple diagnostic hearing tests in a single, convenient system. While many types of diagnostic hearing testing exist, most systems typically are capable of performing only a single test or single type of test. Most audiometer systems, for example, are only capable of performing air-conduction and/or bone-conduction threshold testing. Although some audiometric systems may perform speech recognition testing, there are no commercially available systems capable of conveniently and reliably conducting both audiometric testing and acoustic immittance testing. In addition, there are no systems available for performing both audiometric testing and otoacoustic emission testing.

Inherent in the need for an integrated system for performing multiple diagnostic tests is the need to conduct such tests in a manner that is reliable and convenient for both the hearing health professional and the patient. Merely combining the functionality of an audiometer and an acoustic immittance testing system will provide little benefit if the system is inconvenient to the patient, by for example requiring the patient to use different headphones or ear probes for each test. Instead, there is a need for a system capable of performing multiple diagnostic tests using a single ear probe and an integrated testing system. There is further a need for such systems that are automated to prompt a patient through the tests, while also providing alerts, alarms, notices and other information concerning the tests to a hearing health professional in certain instances.

A convenient multiple diagnostic testing system also implies that the system functionality must be combined in a convenient package that can be quickly and easily coupled to the patient, without a clutter of wires, electrical conduits, transducers and ear probes around the patient. The risk that patient movement would result in damage to one or more wires or conduits in the system is another obstacle to combining multiple diagnostic tests in a single system. In addition, the presence of numerous wires, conduits and probes around the patient can be intimidating and distracting to the patient, in addition to being aesthetically displeasing. Accordingly, there is a need for a system that combines multiple diagnostic tests into a patient interface that can be quickly and easily coupled to the patient, and which provides minimal clutter in the patient environment.

SUMMARY OF THE INVENTION

The present invention provides improved systems for conducting multiple diagnostic hearing tests, and components for performing such tests. As already noted, there is a need in the art for hearing test systems capable of performing audiometric testing and other diagnostic tests such as acoustic immittance tests and otoacoustic emission tests. In addition, components to provide greater reliability and convenience in performing such tests are also desirable. Systems according to the present invention may be automated to minimize the need for monitoring of the tests by hearing health professionals. The systems also desirably provide prompts, alerts or other information to hearing health professionals administering the tests. Reliability of the systems is also enhanced by providing a modular system with calibration data provided as an integral part of certain system components.

In one embodiment, the invention comprises a system for conducting an audiometric test and at least one of, and preferably both of, an acoustic immittance test and an otoacoustic emission test in a first ear of a patient. The system comprises a first insertion probe having a sealing surface for engaging the external auditory canal of the first ear and providing an airtight seal therein. In addition, the system preferably comprises a first transducer for providing an audiometric test sound and at least one of, and preferably both of, an acoustic immittance test sound and an otoacoustic emission test sound to the first ear through the first insertion probe. In the case of otoacoustic emission testing, it is preferred that the first transducer comprise a first otoacoustic transducer element and a second otoacoustic transducer element, each of which provides a test sound at a desired frequency to generate a distortion product otoacoustic emission in the first ear of the patient. The first and second otoacoustic elements may also function to deliver other test tones, e.g., pure tone audiometric tones, to the first ear of the patient.

Where the system is intended to perform tympanometric testing, a reversible compressor is provided to deliver and/or remove a gas, preferably air, to and/or from the first ear through the first insertion probe. The system further comprises a second transducer for receiving at least one of an otoacoustic emission sound and an acoustic immittance test result sound from the first ear through the first insertion probe. In a preferred embodiment, the second transducer is an otoacoustic emission transducer for receiving an otoacoustic emission sound, and the system further comprises a third transducer for receiving an acoustic immittance test result sound selected from the group consisting of a tympanogram test result sound and an acoustic reflex test result sound.

In preferred embodiments of the foregoing system, the first transducer comprises at least one speaker for delivering test sounds to the first ear, and the second and third transducers comprise microphones for receiving, respectively, otoacoustic emission sounds and acoustic emission test result sounds from the first ear. It will be appreciated by persons of skill in the art that more than one speaker may be provided to provide the test sound for each type of hearing test, i.e., an audiometric speaker, an otoacoustic emission speaker (more preferably first and second otoacoustic emission speakers), and an acoustic immittance speaker may each be separately provided. All such speakers together comprise the first transducer, which may also be referred to as a first transducer element for clarity of reference. However, a single speaker, or two speakers if the system includes otoacoustic emission testing, is preferred to minimize cost and complexity of the system. It will also be understood by persons of skill in the art that separate transducers should preferably be provided for receiving the otoacoustic emission sounds and the acoustic immittance test result sounds, because of the large differences in intensity of such sounds, although a single transducer (i.e., microphone) may be used if electronic filtering is capable of resolving each sound.

In a further preferred embodiment, the system comprises at least one, and more preferably two, ambient noise microphones for receiving ambient noise from the patient environment during at least a portion of the hearing test(s). The invention also preferably comprises a bone conduction vibrator that may be coupled to a first portion of the head of the patient, preferably the forehead, for providing a bone conduction hearing test sound to a skull bone of the patient.

For simplicity of illustration, the foregoing system has been described for conducting testing for a first ear of a patient. However, it will be understood that in preferred embodiments the system comprises a second insertion probe, similar to the first insertion probe, for conducting hearing tests in a second ear of the patient. It will also be appreciated that the system preferably comprises a fourth transducer, preferably one or more speakers, for providing audiometric, tympanometric and/or otoacoustic emission test sounds to the second ear through the second insertion probe, and fifth and sixth transducers, preferably microphones, for receiving otoacoustic emission test sounds and acoustic immittance test result sounds, respectively, from the second ear.

Systems of the present invention also preferably provide patient management capabilities. More specifically, systems of the invention comprise a computer that records and compiles the patient responses and test results of the diagnostic hearing tests. The computer preferably analyzes this data and sends an appropriate message to the hearing health professional administering the tests, such as when intervention is needed. For example, when the tests are completed, the patient is not responding or is responding inappropriately, an email, PDA message or, more preferably, a pager message may be sent to the hearing health professional by the system computer.

In another aspect, the invention provides an improved insertion probe for conducting multiple diagnostic tests. As used herein the term "insertion probe" refers to a device for insertion into the external auditory canal of a patient's ear, and which is used for delivering a hearing test sound to an ear of a patient and for receiving and/or transmitting a hearing test result from that ear. Insertion probes of the present invention are to be distinguished from supra-aural earphones, which are worn over the ear, and circumaural earphones, which have foam cushions that fit around the ear, because the insert probes fit within the ear instead of being positioned adjacent to the ear. In addition, insert probes of the invention either include a transducer for receiving a test result sound or transmit a test result sound to such a transducer. Thus, the insert probes may comprise an insert earphone that is inserted into the ear canal (i.e., the external auditory meatus) but the earphone must also comprise either a transducer for receiving a test result sound or a conduit or lumen for transmitting a test result sound to a transducer. As used with respect to the ear probes of the invention, the terms "lumen" and "conduit" are used interchangeably to refer to open cavities or spaces within the ear probe, which generally extend from one surface of the probe to another surface thereof.

Insertion probes of the present invention permit multiple diagnostic hearing tests to be performed with greatly increased convenience to the patient and hearing health professional by facilitating such tests without the necessity of removing the insertion probe and replacing it with another probe or earphone. In one embodiment, the insertion probe can be used to conduct an audiometric hearing test and at least one of an acoustic immittance hearing test and an otoacoustic emission test. Thus, the invention provides an insertion probe capable of being used to conduct an audiometric hearing test and an acoustic immittance hearing test. Alternatively, the invention provides an insertion probe capable of being used to conduct an audiometric hearing test and an otoacoustic emission hearing test.

In a preferred embodiment, an insertion probe of the present invention can be used to conduct an audiometric hearing test, an acoustic immittance hearing test, and an otoacoustic emission hearing test without changing probes and without removing the insertion probe from the ear. In a particularly preferred embodiment, the invention provides an insertion probe usable to perform an audiometric hearing test, a tympanogram, an acoustic reflex test, and an otoacoustic emission test.

The multi-test capability of the insertion probes of the present invention are facilitated by multiple conduits or lumens within the insertion probe that either deliver test sounds to the ear or receive and/or transmit a hearing test result from the ear. At least one conduit is provided for delivering a test sound, such as an air-conduction pure tone of a desired frequency and intensity, to the ear. Where otoacoustic emission testing is to be performed, two conduits are preferred for delivering separately to the ear a first otoacoustic emission test sound and a second otoacoustic emission test sound. At least one additional conduit/lumen is provided to receive and/or transmit a test result to a location outside the ear. In certain embodiments, the test result is received in the conduit as a sound from the ear, such as reflected sound from a tympanogram test or acoustic reflex test, and transmitted by a conduit to a transducer element outside the ear for electronic transmission to a computer for further processing. In systems capable of performing tympanometric tests, at least one conduit/lumen also functions to allow air or another gas to be delivered to or removed from the ear.

In alternate embodiments, systems of the present invention comprise one or more transducer elements within the ear canal itself, medial to the insertion probe. In these embodiments, the transducer receives sound in the ear that is the direct result or output of the test, converts the sound to an electronic signal, and the signal is transmitted through the receiving conduit to a processor remote from the ear. Accordingly, a receiving conduit in an insertion probe of the present invention may transmit sound or electronic signals outside the ear.

Persons of skill in the art will also understand that a transducer may be provided within a conduit, rather than medial or lateral to the insertion probe. In this alternate embodiment, the receiving conduit may initially receive the test result or output as sound energy, which is converted within the conduit to an electrical signal by the transducer, and transmit the signal through the remaining portion of the receiving conduit to a computer.

Although a single receiving conduit may be used to transit multiple test results outside the ear, in preferred embodiments, multiple receiving conduits are preferably provided. It is also preferred that the insertion probe be capable of providing an airtight seal within the ear canal by direct contact. An airtight seal is necessary for conducting a tympanogram test. As used herein, "airtight" refers to a seal having leakage acceptably low for conducting tympanometry testing. It is not required that the seal be completely airproof, with no leakage, but merely that the leakage be sufficiently small to permit tympanometry tests to be conducted on the patient. By providing an airtight seal, insertion probes of the present invention create a pressure chamber within the ear canal between the insert probe and the eardrum. A reversible compressor is preferably provided to either deliver air to the pressure chamber or remove air from the chamber to create the specific pressure conditions necessary for conducting a tympanogram test.

In a further aspect, the invention comprises systems and methods for conducting a hearing test. More particularly, the invention comprises systems and methods for delivering a test sound to an ear of a patient in a test area or test room and measuring the ambient noise in the test area during at least a portion of the hearing test. In contrast to existing hearing test systems, in which the ambient noise levels in the test area are typically measured only at lengthy intervals such as one year, the present invention allows the ambient noise level to be measured and compared to acceptable standards during at least a portion of the actual hearing test for a given patient, i.e., in real time.

In preferred embodiments, the ambient noise level is measured simultaneously with the presentation of each and every test sound provided to the patient, and for the full duration of the test sound presentation interval. If the ambient noise level is not within acceptable levels throughout the test interval, the test sound is presented to the patient again, and the ambient noise is again measured. This process can continue until the ambient noise level is verified as falling within acceptable parameters during the presentation of the test sound, or until a preset number of presentations of the test sound are reached. In such instances, the best recorded threshold is logged and an explanatory note indicating that ambient noise levels exceeded acceptable limits is also included in the diagnostic report.

As used herein, "test area" comprises any area within which the patient is located while the test is conducted. In preferred embodiments, the test area comprises a relatively quiet room. A soundproof chamber of the type used in many hearing tests may also be used, although systems and methods of the invention allow accurate and reliable tests to be conducted without use of a soundproof chamber. The test area may even comprise an open area or, in extremely demanding conductions, outdoors, although such embodiments are not preferred.

Accordingly, in one embodiment, the invention comprises a system for conducting a hearing test on a first ear of a patient, the system comprising a first transducer element for delivering a test sound to the first ear, and a second transducer element for measuring ambient noise in the test area. In preferred embodiments, the first transducer element comprises a non-field speaker, such as a supraaural, circumaural, or insert earphone, for delivering the test sound directly to the ear of the patient. In particularly preferred embodiments the first transducer element is coupled to an insertion probe as previously described. Where field speakers are used, the sound is typically also detected by the second transducer element as ambient noise, which may compromise the effectiveness of the system. It is also preferred that the second transducer element comprise a microphone.

In a still more preferred embodiment, the system comprises a computer with software for temporally coupling the speaker and the microphone to measure ambient noise during the entire pendency of each and every test tone. In preferred embodiments the computer software ensures that the test tone is presented to the patient's ear for a predetermined desired time interval, and that the ambient noise in the test area is measured during at least a portion, preferably the entire duration, of the time interval. Such a testing system essentially independently qualifies (or disqualifies) the test area with each test tone presentation, which provides much greater accuracy and reliability than prior art systems. It will be appreciated, however, that ambient noise need not be measured during the entire pendency of each and every test tone, so long as ambient noise is measuring during at least a portion of some test sounds presented to the patient.

In yet another aspect, the present invention comprises an improved bone conduction hearing test apparatus for testing the bone-conduction hearing threshold of a patient. In one embodiment, the invention comprises an apparatus for engaging the head of a patient to be tested for bone conduction hearing, the apparatus comprising a bone conduction vibrator for contacting a first head portion of the patient, an engagement or contact element for contacting a second head portion of the patient, and a spring to which the bone conduction vibrator and engagement element are coupled. In a preferred embodiment, the spring is a planar spring comprising first and second elements coupled together.

In preferred embodiments, the bone conduction vibrator contacts the forehead of the patient. Although both forehead and mastoid placement are known in the art, forehead placement is more secure generally and is made still more secure, reliable and convenient by the apparatus of the present invention. In a still more preferred embodiment of the present invention, the engagement element is coupled to the rear of the patient's head.

It is preferred that the bone conduction hearing test apparatus provide two-point contact to the patient's head, by which is meant that the apparatus contacts the patient's head at two, and only two, distinct areas, i.e., the first head portion and the second head portion. Although two-point contact bone conduction test elements are known, such systems generally comprise a single spring element. Multiple-element systems are also known, but such systems must be manipulated in three dimensions (i.e., they are not planar) and they are, more importantly, generally unreliable and difficult to use.

In another preferred embodiment, the spring comprises opposed first and second spring elements, with the bone conduction vibrator coupled to the first spring element and the engagement element coupled to the second spring element. Such an arrangement facilitates the desired two-point contact arrangement of the bone conduction hearing test apparatus. In a particularly preferred embodiment, the first and second spring elements are joined at their ends and have opposed middle portions to which the bone conduction vibrator and the engagement element are coupled. This arrangement provides a lenticular-shaped spring when pulled apart that can easily, conveniently and securely be placed on the patient's head.

As referred to herein, "lenticular" refers to a planar, two-sided lens shape having at least one convex side. Thus, lenticular includes both the typical bi-convex lens shape characteristic of a lentil in profile, and also to a mono-convex shape having one convex side and a second side that is either flat (such as the D-shape of an archery bow) or curved. Where the first and second elements have similar elastic (i.e., spring) characteristics, the shape will by a bi-convex shape. Where the first and second elements have different elasticities, the shape will tend towards a more D-shaped lenticular shape. As may be appreciated, where one element is a rigid element, the spring will comprise a D-shape. Other shapes, intermediate between a lentil shape and a D-shape, will be possible where neither element is rigid but where the elasticities differ. The lenticular shape may be conveniently facilitated by hinges coupling the respective end portions of the first and second spring elements. The lenticular-shaped spring is also especially adapted to provide a relatively constant force across a range of patient head sizes, the force ranging from about 1 to 15 newtons, more preferably about 2–6 newtons, and most preferably about 5 newtons.

In another preferred embodiment, the bone conduction hearing test apparatus comprises a spring having first and second contact elements for providing two-point contact to the patient's head, said first contact element comprising a bone conduction vibrator for contacting the patient's head at a first area, preferably the forehead. In a still more preferred embodiment, the spring is a planar, lenticular-shaped spring, and the second contact element comprises an engagement element for engaging the patient's head at a second area, preferably the back of the patient's head.

In still another aspect, the system provides a yoke, wearable around the neck of the patient, for facilitating convenient administration of multiple diagnostic hearing tests to a patient. The complexity of multiple diagnostic hearing tests requires the presence of many conduits, wires, and transducers in the immediate environment of the patient. For safety and reliability, it is desirable to provide a convenient housing for such components. Such a housing is preferably patient-friendly from a convenience and aesthetic perspective.

In one embodiment, the invention comprises a system for conducting multiple diagnostic hearing tests in a first ear of a patient, the system comprising a computer for controlling administration of the multiple diagnostic hearing tests, a plurality of transducers for delivering signals to and receiving signals from said first ear, at least one insertion probe for insertion in the first ear, a plurality of conduits coupling the computer and the plurality of transducers, and a yoke, wearable around the neck of the patient and coupled to the first insertion probe, for providing a housing for the plurality of conduits. Such a yoke both protects the conduits from inadvertent damage during system use and also provides a convenient patient interface with the system.

In preferred embodiments, the system comprises a first and second insertion probes for insertion into the first and second ears of the patient. Where two insertion probes are present, the number of conduits and transducers in the system can be high, and the risk of damage to one or more conduits increases correspondingly. However, the two probes can be conveniently coupled to the yoke on either side of the patient's head, and all of the conduits can be housed within the yoke for protection.

In a particularly preferred embodiment, the system comprises at least one, and more preferably two, ambient noise microphones for monitoring ambient noise during testing and ensuring that it remains within acceptable limits. While the ambient noise microphones may be anywhere in the test area, it is preferred that the ambient noise microphones be provided near the ears of the patient to more closely approximate the noise experienced by the patient. Accordingly, systems of the present invention preferably comprise a wearable yoke to which at least one, and preferably two ambient noise microphones are coupled. The yoke is also conveniently provided with a break therein which may be coupled and decoupled by, for example, Velcro closures for convenience in use and removal by the patient.

BRIEF DESCRIPTION OF THE DRAWINGS

A better understanding of the invention may be had by reference to the following detailed description when taken in conjunction with the accompanying drawings, wherein.

DETAILED DESCRIPTION OF THE INVENTION

Following is a detailed description of the invention with reference to the accompanying drawings, in which reference numerals for the same or similar elements are carried forward.

In one embodiment, the present invention is directed to a method and system for automated testing of a patient's hearing. The term "automated" as used herein refers to testing that is performed primarily by a computer, as opposed to testing that is performed primarily by a hearing health professional. The automated hearing test system preferably is capable of conducting multiple diagnostic hearing tests, and it allows the patient to test his own hearing with minimal or no assistance from an audiologist or other hearing health professionals. The test provides an accurate and thorough assessment of the patient's hearing, including air and bone conduction testing with masking, speech reception threshold, and speech discrimination tests, as well as acoustic immittance testing and otoacoustic emission testing.

Such a patient-administered hearing test system is simpler, more convenient, and less expensive than the traditional audiologist-administered test, while at the same time complying with relevant standards and guidelines such as ANSI requirements or other certification standards. In addition, the automated hearing test system can detect and compensate for ambient noise and, therefore, does not require the use of a certified quiet room or sound isolation booth. Furthermore, the automated hearing test can be configured for any number of languages in order to accommodate patients in every part of the world. Using systems according to the present invention, more people will be able to obtain regular and frequent hearing tests.

Hearing health professionals will also benefit from the automated hearing test of the present invention. Although the test itself requires little or no intervention, a hearing health professional still must analyze the test results and recommend treatment. Therefore, the automated hearing test is presently being made available to the general public through a qualified hearing health professional. The automated hearing test may be offered as a separate service by the hearing health professional, or as part of a more comprehensive service, such as a full physical checkup that patients can obtain annually. Since the test requires little or no intervention, the hearing health professional has more time to treat a larger number of patients and/or spend more time treating each individual patient. Moreover, since the automated hearing test facilitates early detection of hearing loss, the hearing health professional may have a relatively easier time treating certain patients.

Figure 1:
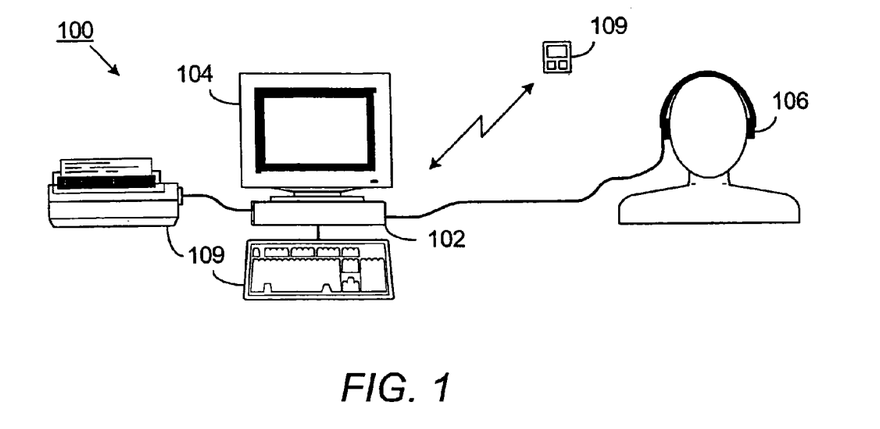
FIG. 1 illustrates an exemplary system for providing an automated hearing test according to embodiments of the invention.

Referring now to FIG. 1, a hearing test system 100 for providing automated hearing tests according to some embodiments of the invention is shown. FIG. 1 is a high level diagram and omits details of the systems of the invention, which are shown in other figures and described more fully hereinafter. The hearing test system 100 shown in FIG. 1 has three primary components, namely, a computer 102 that comprises the functions of one or more hearing test devices, a display screen 104, and an ear engagement element 106. Other components of the system 100 that may be present include a keyboard, mouse, printer, paging device, and the like (indicated generally at 109). The computer 102 may be any suitable computer from a desktop PC to a high-end workstation, or even a PDA, laptop or tablet PC, as the particular type/model/brand of computer is not overly important to the practice of the invention. The display screen 104 may likewise be any suitable display screen from a CRT to a flat-panel LCD, as the particular type/model/brand of display screen is not overly significant for purposes of the present invention. In some embodiments, however, a touchscreen monitor may be easier for a patient to use than conventional CRT for LCD display screens in terms of the physical interaction between the patient and the automated hearing test system, and is preferred in such instances.

Figure 2:
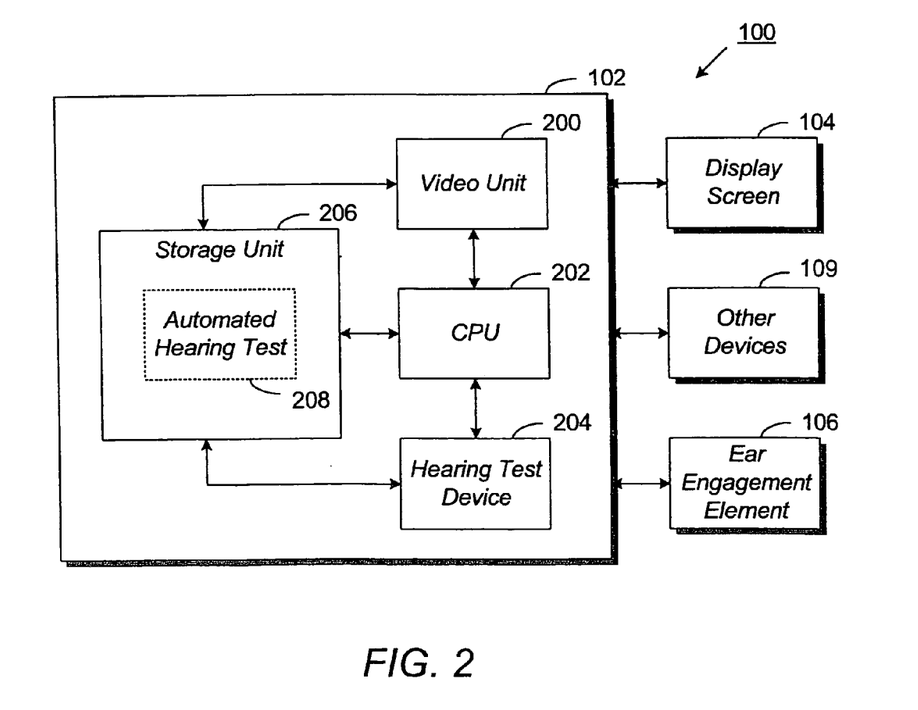
FIG. 2 illustrates a block diagram of the system for providing an automated hearing test according to embodiments of the invention.
Figure 5:
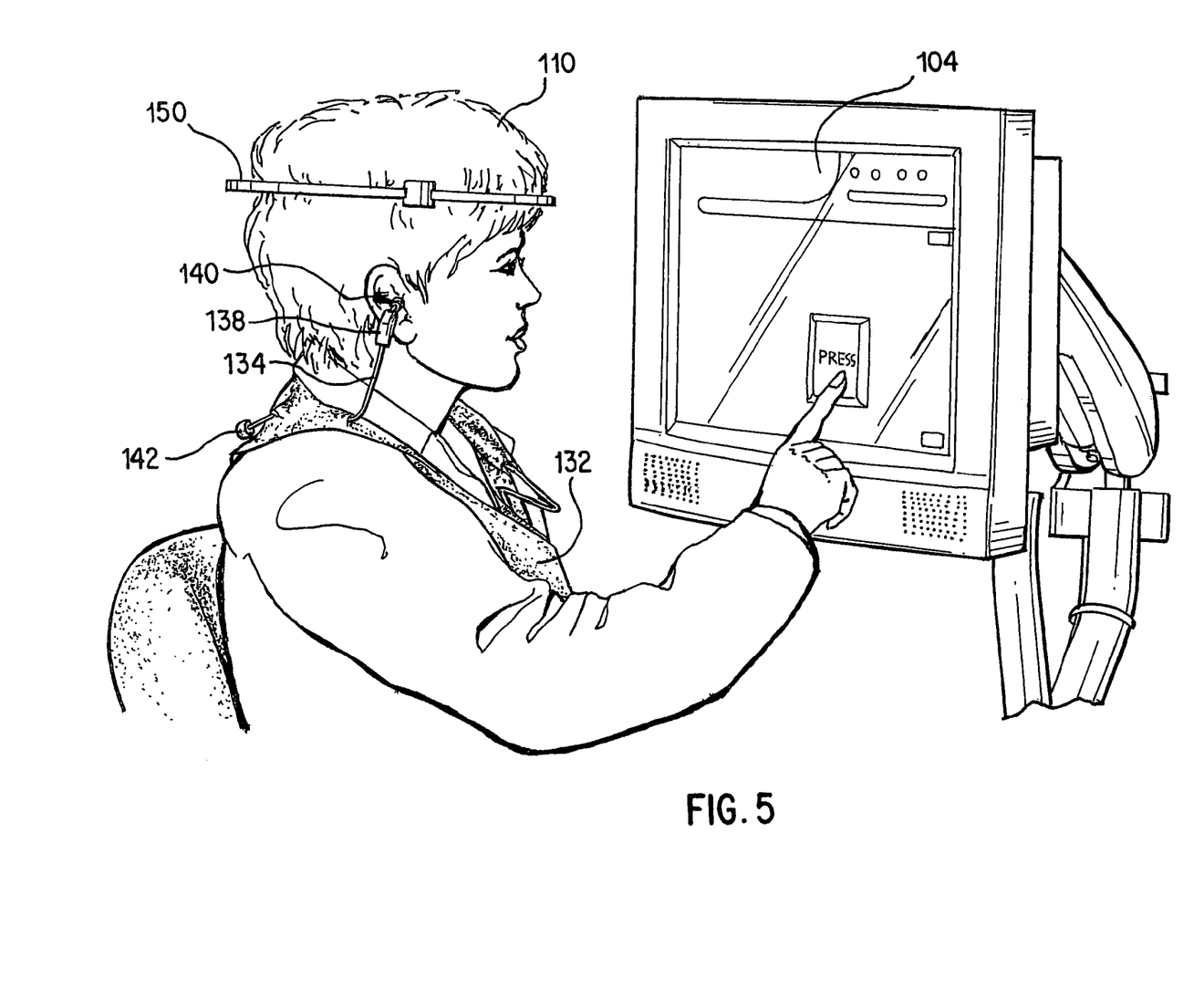
FIG. 5 illustrates a patient using an embodiment of the invention, and wearing a novel bone conduction testing apparatus.
Figure 6:
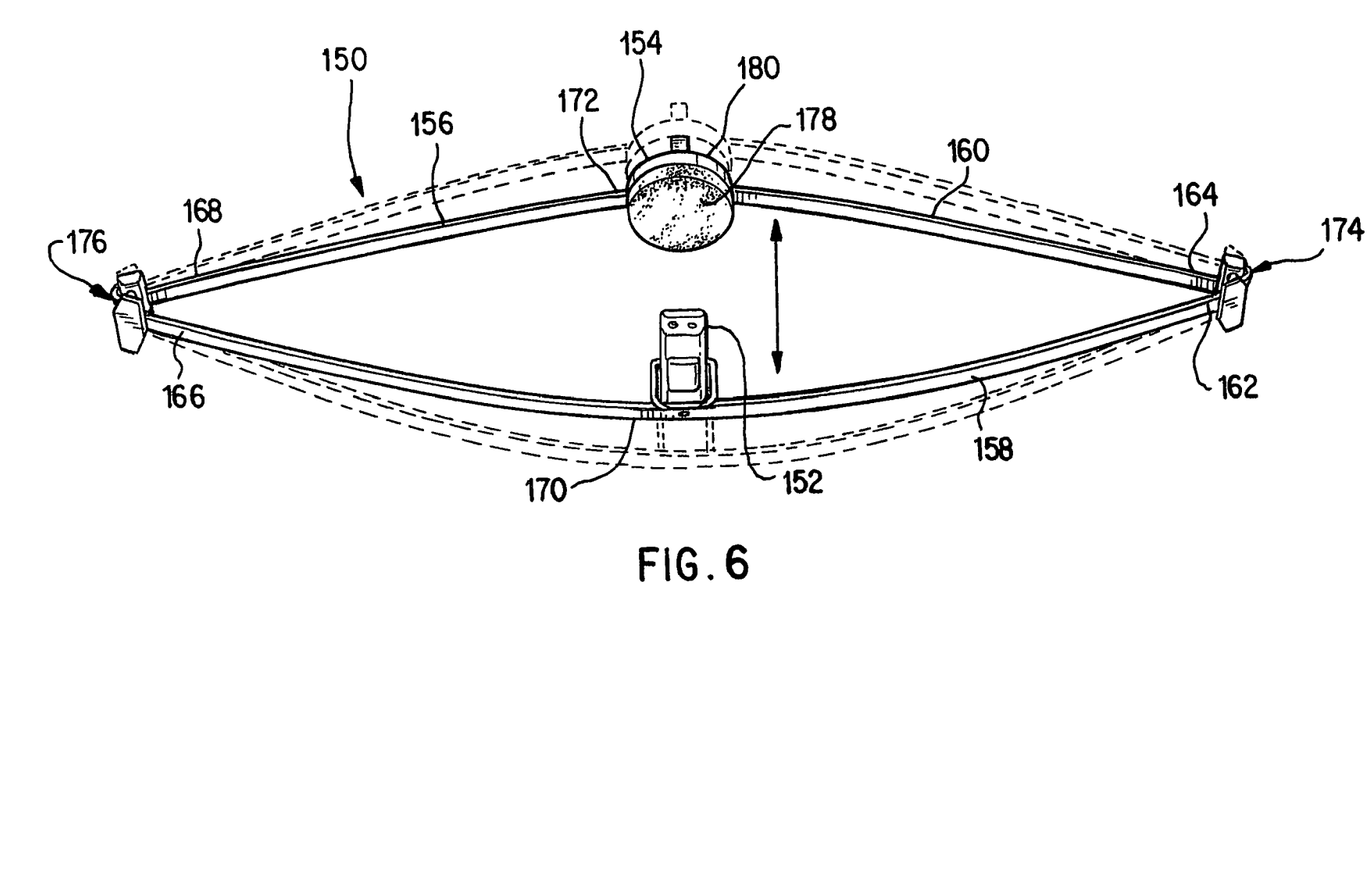
FIG. 6 depicts a bone conduction testing apparatus according to certain aspects of the invention.

Ear engagement element 106 is preferably used for air conduction hearing testing as well as acoustic immittance testing and otoacoustic emission testing. Although referred to in the singular, ear engagement element 106 preferably comprises two coupler elements to facilitate multiple hearing tests in both ears. Ear engagement element 106 may comprise a speaker coupled to a supraaural, circumaural, insert earphone, an ear probe according to the present invention, or other earphones complying with applicable government standards such as, e.g., ANSI S3.6-1996 for delivering the test sound to the ear of the patient. Ear engagement element 106 is preferably coupled to a wearable yoke or vest as depicted generally in FIGS. 3, 5, and 7. Systems of the invention also preferably comprise a bone conduction hearing test sensor such as a bone conduction vibrator. The bone conduction vibrator in systems of the invention is preferably part of a novel bone conduction test apparatus 150, as depicted in FIGS. 5 and 6 and as described more fully hereinafter. FIG. 2 illustrates the system 100 in block diagram form. Computer 102 has a number of functional components, including a video unit 200, a central processing unit 202, a hearing test device 204, and a storage unit 206. These components are well known in the computer art and will therefore be described only briefly here. In general, the video unit 200 provides the video signals that are displayed as images presented to the patient on the display screen 104. In some embodiments, the video unit 200 may be any one of several commercially available video cards. The central processing unit 202 is responsible for the overall operation of the computer 102, including execution of the operating system and any software applications residing on the computer 102. In some embodiments, the central processing unit 202 may be any one of several commercially available microprocessors. The audio unit 204 provides the audio signals that are converted into the various tones and speech by the ear engagement element 106. Hearing test device 204 may comprise any or all of an audiometer, an otoacoustic emission test device, a tympanometer, a masking noise generator, or other known hearing test devices. Alternatively, electronic circuit boards performing the functionality of such test devices may also be used. The storage unit 206 provides long-term and temporary (i.e., caching) storage for the software and data that are used by the computer 102 and may include one or more of, for example, a hard drive, main memory, removable storage (e.g., CD-ROM, floppy disk), and the like.

In some embodiments, the storage unit 206 also stores the automated hearing tests of the present invention, indicated at 208. More specifically, the storage unit 206 stores a computer-readable version of the automated hearing tests 208, which preferably include audiometric tests, acoustic immittance tests, and otoacoustic emission tests, that can be executed by the computer 102, and in particular the hearing test device 204. During execution, a portion of the hearing test computer programs 208 may be temporarily loaded from, for example, the hard disk and into the main memory components of the storage unit 206. In addition to the stand-alone arrangement, it is also possible to execute the automated hearing test programs 208 from a computer network. For example, the automated hearing test programs 208 may be stored on a server computer (not expressly shown) that is accessible to several client computers. This arrangement has an advantage in that updates to the automated hearing test programs 208 may be quickly and easily implemented. Other environments for executing the automated hearing test programs 208 may also be used without departing from the scope of the invention.

The source code for the automated hearing test programs 208 may be written in any suitable programming language (e.g., C, C++, Visual Basic, and other computer languages). It has been found, however, that object oriented programming languages such as C++ and Visual Basic can result in a somewhat more efficient program. In addition, the automated hearing test programs 208 can be implemented using a number of different programming methodologies. The particular programming methodology as well as the particular programming language used are not overly important considerations for the practice of the invention. In one embodiment, the methodology of the automated hearing test programs 208 involves a plurality of individual modules or subroutines that can be called to perform specific functions. The modules or subroutines can be called from a main routine and from within other modules or subroutines. The subroutines can pass data to and from each other as well as to and from the main routine.

Systems of the invention are capable of conducting multiple diagnostic hearing tests in a user-friendly manner, while minimizing the need for extensive supervision and monitoring of the tests by a hearing health professional. In particular, systems of the invention are capable of conducting both air-conduction and bone-conduction audiometry hearing tests on a patient (and also preferably speech audiometry including speech recognition threshold and speech discrimination tests), plus at least one additional test that is either an acoustic immittance test or an otoacoustic emission test. The systems are capable of sending a diagnostic message, e.g., an email, PDA message or pager message to a hearing health professional should there by a need for intervening in the tests, or to signal completion thereof.

Many types of diagnostic hearing tests are known. As used herein, the terms "audiometry," "audiometric testing," and/or "audiometric tests" may be used interchangeably to refer to testing that includes threshold testing to determine the lowest sound pressure level that a patent may hear either pure tones at specific frequencies, or recognize and/or distinguish speech. Details of audiometric testing are known in the art, and certain aspects thereof are described at, e.g., Gelfand, S., *Essentials of Audiology*, 2d ed., chapters 3,4, Thieme Medical Publishers, Inc. (2001).

The terms "acoustic immittance testing," and "acoustic immittance tests" are used interchangeably to refer to testing that measures the impedance to sound flow or, conversely, the ease with which sound flows through the hearing system of the patient. Acoustic immittance tests include tympanometric testing, in which the ear canal is pressurized, usually with air, and the immittance of the ear is measured at various pressures as air is removed from the ear. Such testing is used to determine whether components of hearing loss are attributable to the outer ear or the middle ear. Acoustic immittance tests also include acoustic reflex testing, which as used herein refers to testing that measures the immittance changes in the ear that occur reflexively in response to a sufficiently intense sound. Details of acoustic immittance testing are known in the art, and certain aspects thereof are described at, e.g., Gelfand, S., *Essentials of Audiology*, 2d ed., chapters 7, 11 Thieme Medical Publishers, Inc. (2001).

Otoacoustic emission testing refers to testing that measures sounds produced by the cochlea of the ear, which are known as otoacoustic emissions (OAEs). Many types of otoacoustic emissions are known, including spontaneous OAEs, evoked OAEs, and distortion product OAEs. As used herein, the terms "otoacoustic emission tests," and "otoacoustic emission testing" refer to testing that measures any of the foregoing types of otoacoustic emissions, particularly distortion product otoacoustic emissions, which can provide information on certain types of hearing loss. Details of otoacoustic emission testing are known in the art, and certain aspects thereof are described at, e.g., Gelfand, S., *Essentials of Audiology*, 2d ed., chapters 7, 11 Thieme Medical Publishers, Inc. (2001). Other references providing additional details on audiometric, acoustic immittance, and otoacoustic emission tests are readily available.

Figure 3:
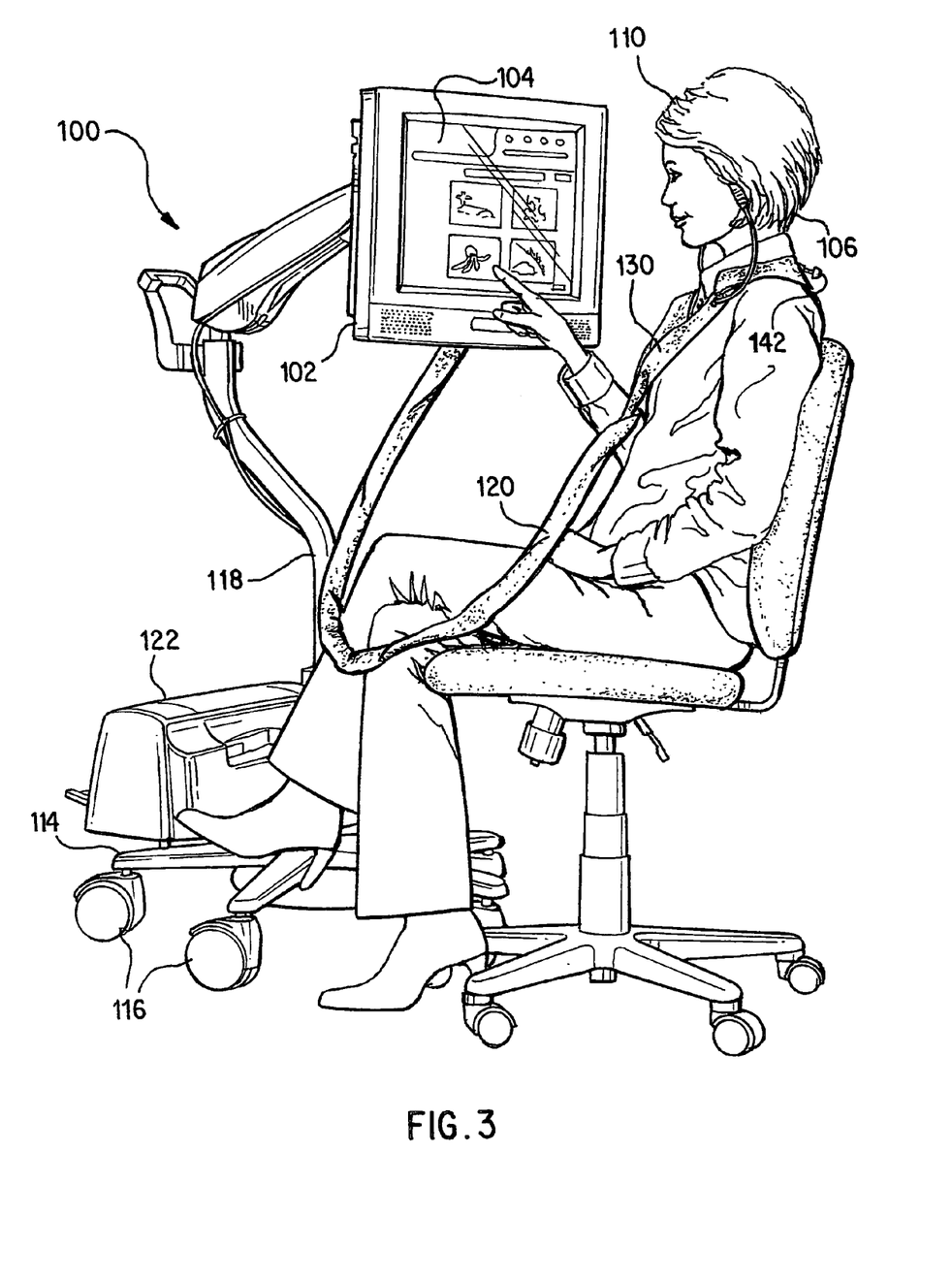
FIG. 3 illustrates a system for conducting multiple hearing tests according to embodiments of the invention, in use by a patient.
Figure 4:
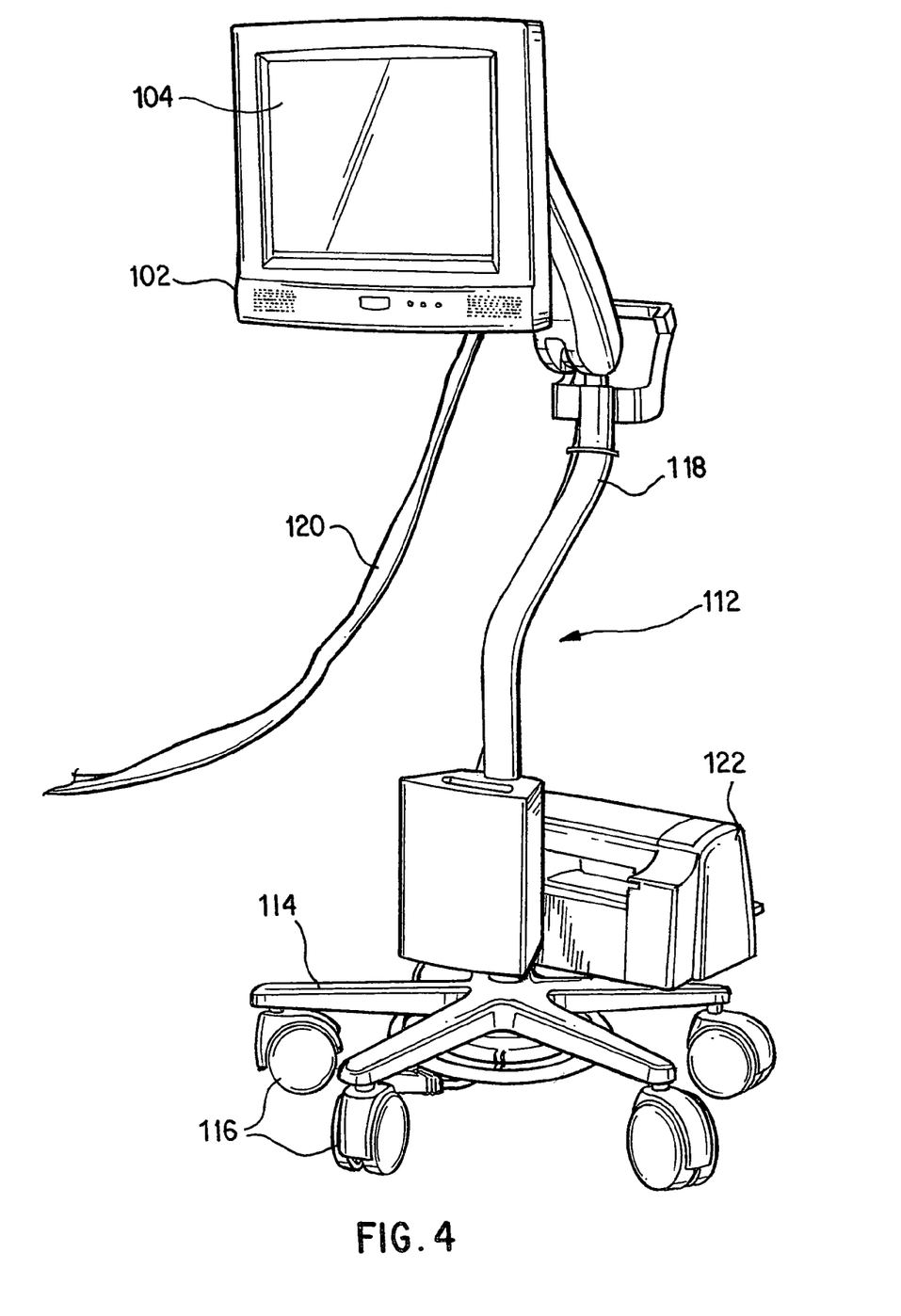
FIG. 4 illustrates a cart and user interface for use in a system according to an embodiment of the invention.

A system embodying certain preferred aspects of the invention is depicted in FIGS. 3 and 4. FIG. 3 illustrates a patient 110 using an embodiment of a computer-controlled system 100 for conducting multiple diagnostic hearing tests. FIG. 4 depicts portions of the system 100 that are interfaced with the patient 110 via cable conduit 120 and display screen 104. In general, in these figures a hearing test system 100 is provided for administering multiple diagnostic hearing tests, including preferably audiometric, acoustic immittance, and otoacoustic emission tests. The system 100 comprises a computer 102, preferably located in the same housing as the display screen 104, conveniently mounted on a support arm 118 of a cart 112. The support arm 118 is preferably adjustable to allow the height of the display screen 104 to be customized to the height of the patient 110. A plurality of wheels 116 is preferably provided on a base 114 of cart 112 to provide mobility to the system 100. Display screen 104, preferably a touch-sensitive display screen as shown, is provided to facilitate testing and patient response. A printer 122 is provided on base 114 to provide printouts of test results.

It should also be appreciated that alternative embodiments different in construction and appearance from the mobile cart system depicted in FIGS. 3 and 4 are also within the scope of the invention. In particular, systems may comprise stationary systems in a physician's office, or laptop and/or mobile systems that may be moved from location to location to serve a wide patient population.

Figure 7:
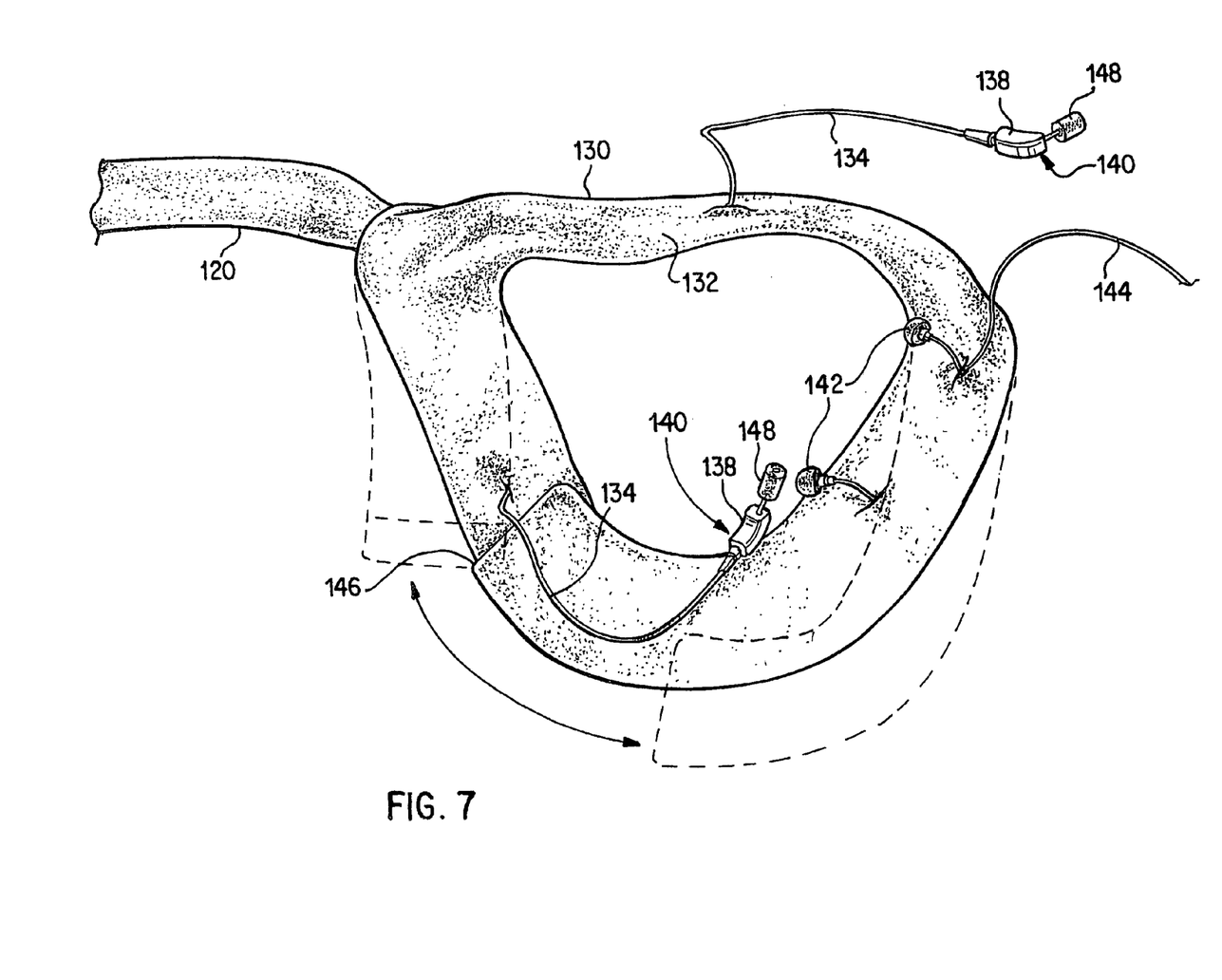
FIG. 7 depicts a wearable yoke according to one aspect of the invention, and depicting a detachable coupling allowing ease of patient use.

As illustrated in FIGS. 3, 5, and 7, the system preferably comprises a wearable yoke or vest 130 that may be worn around the patient's neck during the test. The patient may be seated comfortably in a suitable seat (not numbered) adjacent to the touch-screen 104 while the multiple diagnostic hearing tests are administered. Yoke 130, and more particularly the components electrically or otherwise coupled thereto, is coupled to the computer 102 via cable conduit 120.

As shown in greater detail in FIG. 7, which illustrates an embodiment of a yoke suitable for use in systems of the invention, yoke 130 provides a flat, conduit-like housing 132 for the electrical cables and other conduits, such as an air conduit (not shown) for use in tympanometry testing. A plurality of slits or similar openings (not numbered) are provided in housing 132 of yoke 130 to allow conduits 134 for insertion probe elements 140 to extend from the housing 132 to the ears of the patient 110. Insertion probe elements 140 generally comprise at least an insertion probe tip 148 and a transducer 138. The transducer 138 may be external and separate from probe tip 148, or may be incorporated into it. The insertion probe elements 140 may comprise multiple transducers, including one or more speaker elements and one or more receiver elements, e.g., a microphone. The yoke may also be used to house additional components of the system to make the system more independent of the computer platform. In particular, electronic circuit boards or cards embodying the functionality of an audiometer, an otoacoustic emission test device, a tympanometer, and/or an acoustic reflex test device may also be provided and housed within the yoke. By this means the systems may be used in connection with a wider range of computer terminal devices. The yoke may also, in preferred embodiments, include a memory element storing calibration data for the transducers (i.e., speakers and microphones) used in the system to allow a computer 102 to generate appropriately calibrated signal tones.

In a particularly preferred embodiment, the system comprises at least one, and more preferably two, ambient noise microphones for monitoring ambient noise during testing and ensuring that it remains within acceptable limits. While the ambient noise microphones may be anywhere in the test area, it is preferred that the ambient noise microphones be provided near the ears of the patient to more closely approximate the noise experienced by the patient. Accordingly, systems of the present invention preferably comprise a wearable yoke to which at least one, and preferably two, ambient noise microphones are coupled. The yoke is also conveniently provided with a break 146 therein which may be coupled and decoupled by, for example. Velcro closures for convenience in use and removal by the patient. In a preferred embodiment, at least one ambient noise microphone 142, and preferably two, ambient noise microphones also extend through slits or openings in yoke 130 to monitor ambient noise during at least a portion of the multiple diagnostic hearing tests. A wire or cable 144 also extending through an opening in yoke 130 couples the yoke to a novel bone conduction apparatus 150.

FIG. 5 depicts a patient using the novel bone conduction apparatus 150 in conjunction with the system of FIGS. 3 and 4. FIG. 6 illustrates the novel bone conduction apparatus in greater detail. In general, the invention provides an improved bone conduction test apparatus 150. The apparatus 150 is generally planar, and provides two-point contact on a patient's head. "Two-point contact" as used herein, means that the apparatus provides contact on two, and only two, particular locations on the head. Such locations are well-defined and specific, as opposed to general contact areas such as along a headband or like means of contacting an extensive linear or areal portion of the head of the patient.

Returning to FIGS. 5 and 6, the apparatus 150 preferably comprises a bone vibrator 152, known generally in the art, for engaging the head at a first location, preferably the forehead. Apparatus 150 further comprises an engagement element 154 for engaging the head at a second location, preferably the back of the head. Engagement element 154 may comprise a rigid portion 180, made of hard plastic or like material, and a foam member 178 that directly contacts the second location of the head. Finally, apparatus 150 comprises a lenticular spring 156 to which the bone conduction vibrator 152 and engagement element 154 are coupled. Apparatus 150 enables two-point contact by using the bone conduction vibrator 152 as a first contact element and the engagement element 154 as a second contact element.

Lenticular spring 156 is preferably made by joining opposed first and second spring elements 158 and 160. Each of the first and second spring elements further comprises a first end, a middle portion, and a second end. Thus, first spring element 158 comprises a first end portion 162, a middle portion 170, and a second end portion 166. Similarly, second spring element 160 comprises a first end portion 164, a middle portion 172, and a second end portion 168. The first and second spring elements 158 and 160 are joined at their first end portions 162 and 164 at a first joint or connection 174, and at their second end portions 166 and 168 at a second joint or connection 176. The joints/connections 174 and 176 may comprise any known means of joining such as riveting, soldering, and other types of metal fastenings. In a particularly preferred embodiment, joints 174 and 176 both comprise hinge connections as depicted in FIG. 6. Bone conduction vibrator 152 and engagement element 154 are preferably coupled to middle portions 170 and 172, respectively, of first and second spring elements 158 and 160.

The construction of the bone conduction apparatus 150 as depicted in FIGS. 5 and 6 provides a lenticular-shaped spring 156 that can be easily pulled apart at the middle portions 170 and 172, and thereby easily and securely coupled to the patient's head for performing bone conduction hearing testing. Lenticular-shaped spring 156 is also especially adapted to provide a relatively constant force across a range of patient head sizes, the force ranging from about 1 to 15 newtons, more preferably about 2–6 newtons, and most preferably about 5 newtons.

While it is preferred that both the first and second spring elements 158, 160 have identical or very similar elastic characteristics, in alternate embodiments at least one element, preferably second spring element 160, may be less elastic than the other spring element. In one alternative embodiment, the second spring element comprises a rigid linear member, resulting in a D-shaped lenticular spring (not shown). Other embodiments, in which the second spring element is not rigid, but is less elastic than the first spring element, are also possible.

In another embodiment, a thin, flexible member such as a ribbon or cloth (not shown) may be coupled to the second contact element 154 and extended over the top of the patient's head to a point on the patient's forehead. The bone vibrator may then contact the ribbon or cloth, which may comprise a tacky or texturized surface to provide more secure seating for the bone vibrator. Such a member is particularly useful in cases of anatomical irregularities or oily skin. In another aspect, the invention provides an improved ear probe element for conducting multiple diagnostic tests. The improved ear probe element of the present invention allows multiple diagnostic hearing tests to be conducted without removing the ear probe element from the ear being tested. This is in contrast to currently available systems, which generally use different ear probe elements to performing, e.g., audiometric, acoustic immittance, and otoacoustic emission tests.

The improved ear probe element of the present invention comprises an insertion probe element. The terms "insertion probe" and "insertion probe element" refer to a device for insertion into the external auditory canal of a patient's ear, and which is used for delivering a hearing test sound to an ear of a patient and for receiving and/or transmitting a hearing test result from that ear. Because they comprise at least a tip portion that fits within the ear instead of being positioned adjacent to it, insertion probes of the present invention are to be distinguished from supra-aural and circumaural earphones, which engage the outer part of the ear (i.e., the pinna). In addition, insertion probes of the present invention either include within the element a transducer (e.g., a microphone) for receiving a test result sound, or transmit a test result sound to such a transducer via a conduit within the insertion probe.

Figure 8:
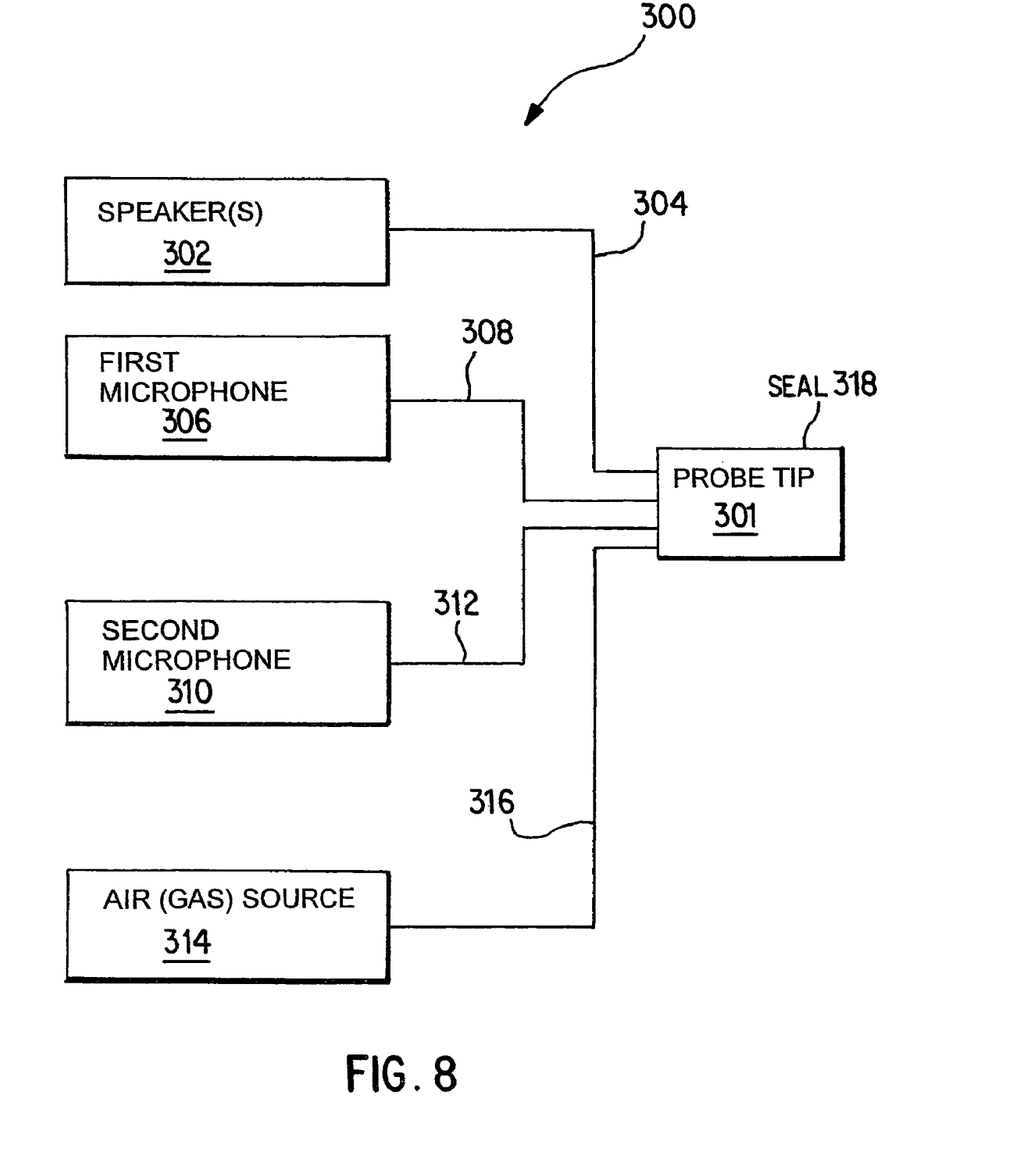
FIG. 8 is a block diagram of an ear probe element according to an embodiment of the invention.

The multi-test capability of the insertion probes of the present invention are facilitated by multiple conduits within the probe that either deliver test sounds to the ear or receive and/or transmit a hearing test result from the ear. FIG. 8 is a block diagram illustrating such an insertion probe 300. In particular, the insertion probe element comprises an insertion probe tip 301 that is actually inserted into the external auditory canal of the patient. The insertion probe comprises a plurality of transducers coupled to insertion probe tip 301, such as a speaker 302, and first and second microphones 306 and 310.

In the embodiment illustrated in FIG. 8, the speaker 302 and microphones 306 and 310 are shown as separate elements from insertion probe tip 301, coupled thereto via speaker conduit 304, first microphone conduit 308, and second microphone conduit 312, respectively. In one embodiment, first microphone 306 is a microphone for receiving an otoacoustic emission sound from an ear being tested and conduit 308 is a conduit for transmitting the otoacoustic emission sound, while second microphone 310 is an acoustic immittance microphone for receiving a tympanometric test result sound and/or an acoustic reflex test result sound, and conduit 312 is a conduit for transmitting the tympanometric and/or acoustic reflex test result sound. However, in other embodiments (not shown), one or more of the transducers may be provided as a part of insertion probe tip 301. In addition, multiple speakers may be provided for providing different test sounds to a patient, i.e., audiometric threshold test tones, otoacoustic emission test tones, and tympanometric and/or acoustic reflex test tones.

The insertion probe element 300 shown in FIG. 8 also provides a gas source 314, which is preferably a reversible air compressor, for introducing and removing air from the ear of the patient. Gas source 14 is coupled to insertion probe tip 301 via air conduit 316. Insertion probe element 300 also comprises a seal 318 to prevent excess air leakage into or from the ear of the patient. The seal provides an airtight seal, which as used herein refers to a seal having leakage acceptably low for conducting tympanometry testing. Thus, it is not required that the seal provide a completely airproof seal with no leakage, but merely that the leakage be sufficiently small to permit tympanometry tests to be conducted on the patient.

By providing an airtight seal, insertion probes 300 of the present invention create a pressure chamber within the ear canal between the insert probe and the eardrum. A reversible compressor is preferably provided to either deliver air to the compression chamber or remove air from the chamber to create the specific pressure conditions necessary for conducting a tympanogram test.

It may be appreciated by persons of skill in the art that one or more of the foregoing conduits 304, 308, 312, 316 may be combined into a single conduit. Alternatively, individual transducers and gas sources may each have separate conduits passing through the probe tip. In preferred embodiments, at least one conduit, such as speaker conduit 304, is provided for delivering a test sound, such as an air-conduction pure tone of a desired frequency and intensity, to the ear. Where otoacoustic emission testing is to be performed, it is preferred that two speakers, each having separate conduits, be provided to minimize distortion of the two sounds used for OAE testing prior to the sounds entering the ear canal.

At least one additional conduit, such as conduits 308 and 312, is provided to receive and/or transmit a test result to a location outside the ear. Although a single receiving conduit may be used to transit multiple test results outside the ear, in preferred embodiments, multiple receiving conduits are preferably provided.

In certain embodiments of the insertion probe 300, the test result is received in the conduit as a sound from the ear, such as reflected sound in a tympanogram test or acoustic reflex test, and the sound is transmitted by a conduit to a transducer element outside the ear for electronic transmission to a computer for further processing.

In alternate embodiments (not shown), insertion probe 300 comprises one or more transducer elements within the ear canal itself, medial to the probe tip 301. In these embodiments, the transducer (e.g., microphones 306, 310) receives sound in the ear that is the direct result or output of the test, converts the sound to an electronic signal, and the signal is transmitted through the probe tip 301 and receiving conduit (e.g., 308, 312) to a processor remote from the ear. Accordingly, a receiving conduit in an insertion probe of the present invention may transmit either sound or electronic signals through the probe tip 301 outside the ear.

Persons of skill in the art will also understand that a transducer may be provided within the probe tip 301, rather than medial or lateral to it. In this alternate embodiment (not shown), the receiving conduit may initially receive the test result or output as sound energy, which is converted within the conduit (and within probe tip 301) to an electrical signal by the transducer, and the signal is then transmitted as an electrical signal through the remaining portion of the receiving conduit to a computer.

As noted, insertion probes 300 of the present invention permit multiple diagnostic hearing tests to be performed without removing the insertion probe and replacing it with another probe or earphone. In one embodiment, the insertion probe 300 can be used to conduct an audiometric hearing test and at least one of an acoustic immittance hearing test and an otoacoustic emission test. Thus, the invention provides an insertion probe 300 capable of being used to conduct an audiometric hearing test and an acoustic immittance hearing test. Alternatively, the invention provides an insertion probe capable of being used to conduct an audiometric hearing test and an otoacoustic emission hearing test.

In a preferred embodiment, an insertion probe of the present invention can be used to conduct an audiometric hearing test, an acoustic immittance hearing test, and an otoacoustic emission hearing test without changing probes and without removing the insertion probe from the ear. In a particularly preferred embodiment, the invention provides an insertion probe usable to perform an audiometric hearing test, a tympanogram, an acoustic reflex test, and an otoacoustic emission test.

In a further aspect, the invention comprises systems and methods for conducting a hearing test. More particularly, the invention comprises systems and methods for delivering a test sound to an ear of a patient and measuring the ambient noise in the test area during at least a portion of one or more of the multiple diagnostic hearing tests. In contrast to existing hearing test systems, in which the ambient noise levels in the test area are typically measured and only certified periodically, and then not during hearing testing, the present invention allows the ambient noise level to be measured and compared to acceptable standards during at least a portion of the actual hearing test for a given patient.

In preferred embodiments, the ambient noise level is measured simultaneously with the presentation of every test sound presented to the patient. If the ambient noise level is unacceptably high during the presentation of the test sound, the test sound is presented to the patient again, and the ambient noise is again measured. This process continues until the ambient noise level is within acceptable parameters during the presentation of the test sound, or until a preset number of presentations of the test sound are reached. In the latter instance, the best recorded threshold is logged and an explanatory note is included in the test results report indicated that ambient noise exceeded acceptable levels.

As illustrated in FIGS. 3, 5 and 7, in one embodiment, the invention comprises a system for conducting a hearing test on a first ear of a patient, the system comprising a first transducer element 138 for delivering a test sound to the first ear, and at least a second transducer element 142 for measuring ambient noise in the test area. In preferred embodiments, the sound is delivered to the ear by an insert probe element 140 or other non-field speaker. Where field speakers are used, the sound is typically also detected by the second transducer element as ambient noise, which may compromise the effectiveness of the system. It is also preferred that the second transducer element 142 comprise a microphone.

In a still more preferred embodiment, the system comprises a computer with software in computer 102 for coupling the transducer 138 and the microphone 142 to simultaneously measure ambient noise via microphone 142 during the entire period of presentation of the test tone to the ear. In preferred embodiments the computer software ensures that the test tone is presented to the patient's ear for a predetermined desired time interval through transducer 138 and insertion probe element 140, and that the ambient noise in the test area is measured during at least a portion, preferably the entire duration, of the time interval through microphone 142. Such a testing system essentially independently qualifies (or disqualifies) the test area with each test tone presentation, which provides much greater accuracy and reliability than prior art systems. It will be appreciated, however, that ambient noise need not be measured during the entire pendency of each and every test tone, so long as ambient noise is measured during at least a portion of some test sounds presented to the patient. In an alternate embodiment, the ambient noise measurement may be made during a portion of the test that is not part of the presentation of the test sounds, such as immediately before or after the test sounds are presented. Indeed, even measuring the ambient noise immediately prior to conducting the hearing tests on the patient is permissible and represents and significant improvement over prior art practices, which do not involve ambient noise measurement proximate in time to actual hearing testing of patients.

It will be appreciated that many alterations, modifications and changes may be made by persons of skill in the art to the systems and components described herein. Such changes are deemed to be within the scope and spirit of the invention, as measured by the claims hereinafter.

What is claimed is:

1. A bone conduction hearing test apparatus for engaging the head of a patient to be tested for bone conduction hearing, comprising:
   a bone conduction vibrator for contacting a first head portion of the patient;
   an engagement element for contacting a second head portion of the patient, and
   a planar spring comprising opposed first and second spring elements, wherein said bone conduction vibrator and said engagement element are coupled to said planar spring.

2. The bone conduction hearing test apparatus of claim 1, wherein said bone conduction vibrator is a forehead bone conduction vibrator.

3. The bone conduction hearing test apparatus of claim 2, wherein said engagement element is capable of engaging the back of the head of said patient.

4. The bone conduction hearing test apparatus of claim 2, wherein said apparatus engages the head of the patient at only said first head portion and said second head portion.

5. The bone conduction hearing test apparatus of claim 3, wherein said spring is capable of providing a force of from about 0 to 15 newtons to maintain contact between said forehead bone conduction vibrator and said first head portion.

6. The bone conduction hearing test apparatus of claim 3, wherein said bone conduction vibrator is coupled to said first spring element and said engagement element is coupled to said second spring element.

7. The bone conduction hearing test apparatus of claim 6, wherein said first and second spring elements each comprise a first end, a second end, and a middle portion, said first ends being coupled together at a first joint, said second ends being coupled together at a second joint, and said middle portions forming a lenticular shaped spring when pulled apart.

8. The bone conduction hearing test apparatus of claim 1, wherein said bone conduction hearing test apparatus engages the head of the patient at only said first head portion and said second head portion.

9. The bone conduction hearing test apparatus of claim 8, wherein said first head portion is a portion of the forehead of the patient.

10. The bone conduction hearing test apparatus of claim 8, wherein said second head portion is a portion of the back of the patient's head.

11. A bone conduction hearing test apparatus for engaging the head of a patient to be tested for bone conduction hearing, said apparatus comprising:
   a lenticular-shaped spring; and
   a bone conduction vibrator coupled to said lenticular-shaped spring, wherein said spring provides a force to maintain contact between said bone conduction vibrator and a first head portion of the patient.

12. The bone conduction hearing test apparatus of claim 11, wherein said first head portion is a portion of the forehead of the patient.

13. A bone conduction hearing test apparatus for engaging the head of a patient to be tested for bone conduction hearing, said apparatus comprising:
a lenticular-shaped spring, comprising opposed first and second spring elements each having a first end, a second end, and a midsection, said first ends being coupled together at a first connection, said second ends being coupled together at a second connection, and said midsections developing a spring force when pulled apart to form a lenticular shape; and
a bone conduction vibrator for engaging a first head portion of the patient and an engagement element for engaging a second head portion of the patient, said bone conduction vibrator being coupled to said first spring element and said engagement element being coupled to said second spring element.

14. The bone conduction hearing test apparatus of claim 13, wherein said lenticular-shaped spring is capable of providing a force of from about 0 to 15 newtons to maintain contact between said bone conduction vibrator and said first head portion.

15. The bone conduction hearing test apparatus of claim 13, wherein said first head portion is a portion of the forehead of the patient.

16. The bone conduction hearing test apparatus of claim 13, wherein said second head portion is a portion of the back of the patient's head.

17. The bone conduction hearing test apparatus of claim 13, wherein said bone conduction hearingtest apparatus engages the head of the patient at only said first head portion and said second head portion.

18. An apparatus for bone conduction hearing testing of a patient, said apparatus comprising a lenticular-shaped spring having first and second contact elements for contacting the patient's head at only two distinct areas, said first contact element comprising a bone conduction vibrator for contacting the patient's head at a first area.

19. The apparatus of claim 18, wherein said second contact element comprises an engagement element for contacting the patient's head at a second area.

20. The apparatus of claim 19, wherein said engagement element comprises a rigid portion.

21. The apparatus of claim 18 wherein said bone conduction vibrator is a forehead bone conduction vibrator.

22. The apparatus of claim 18, wherein said lenticular-shaped spring comprises opposed first and second spring elements each having a first end, a second end, and a midsection, said first ends being coupled together at a first connection, said second ends being coupled together at a second connection, and said midsections developing a spring force when pulled apart.

23. The apparatus of claim 22, wherein said bone conduction vibrator is coupled to said first spring element and said second contact element is coupled to said second spring element.

24. The apparatus of claim 19, wherein said second area is a portion of the back of the patient's head.

25. The apparatus of claim 22 wherein said force is about 5.4 newtons.

26. The apparatus of claim 18 wherein said lenticular-shaped spring is adapted to provide a relatively constant force across a range of patient head sizes.

27. The apparatus of claim 22 wherein said opposed first and second spring elements have the same or different elasticities.

28. The apparatus of claim 18 wherein said apparatus is adapted for deterring attenuation of a bone-conduction signal when said apparatus is used for bone conduction testing.

* * * * *